United States Patent [19]

Davis, Jr. et al.

[11] Patent Number: 4,519,982

[45] Date of Patent: May 28, 1985

[54] TWO DIMENSIONAL MICROWAVE CHEMICAL FLOOD TESTING MEANS AND METHOD

[75] Inventors: Lorne A. Davis, Jr.; Helen K. Haskin, both of Houston, Tex.

[73] Assignee: Texaco Inc., White Plains, N.Y.

[21] Appl. No.: 357,922

[22] Filed: Mar. 15, 1982

[51] Int. Cl.$^3$ .............................................. E21B 49/00
[52] U.S. Cl. ..................................... 422/68; 166/252; 324/58.5 A
[58] Field of Search ................................ 166/252, 66; 324/58.5 A, 376; 422/68; 436/31; 250/252, 255, 250/261, 269

[56] References Cited

U.S. PATENT DOCUMENTS 4,301,400  11/1981  Paap ............................... 324/58.5 A

OTHER PUBLICATIONS

Parsons, Society of Petroleum Engineers Journal, 8/75, pp. 302–309.
Velmex, Unislide Motor Driven Assemblies, Catalogue M-83, 1960.

*Primary Examiner*—Hiram H. Bernstein
*Attorney, Agent, or Firm*—Robert A. Kulason; Ronald G. Gillespie

[57] ABSTRACT

A method of two dimensional chemical flood testing includes evacuating a porous medium contained in a test cell. The porous medium in the test cell is irradiated with a beam of microwave energy at a plurality of predetermined locations on said test cell. The microwave energy that has passed through the porous medium at each location is detected at the location. The porous medium in the test cell is filled with brine. The irradiating and detecting steps are repeated, the porous medium is then flooded with crude oil, or a substitute, and again the irradiating and detecting steps are repeated. The porous medium is flooded with brine and again the irradiating and detecting steps are repeated. A calibration curve for each location is derived from the detected microwave energy at the location from the prior irradiating and detecting steps. The chemical flood system is tested by flooding the porous medium with the chemical flood system at a predetermined flow rate during which time the irradiating and detecting steps are repeated periodically so that the test cell is periodically scanned in two directions by microwave energy. A two dimensional pattern of the chemical flood is derived for each scan in accordance with the detected microwave energy at each location for the scan and the calibration curves.

5 Claims, 6 Drawing Figures

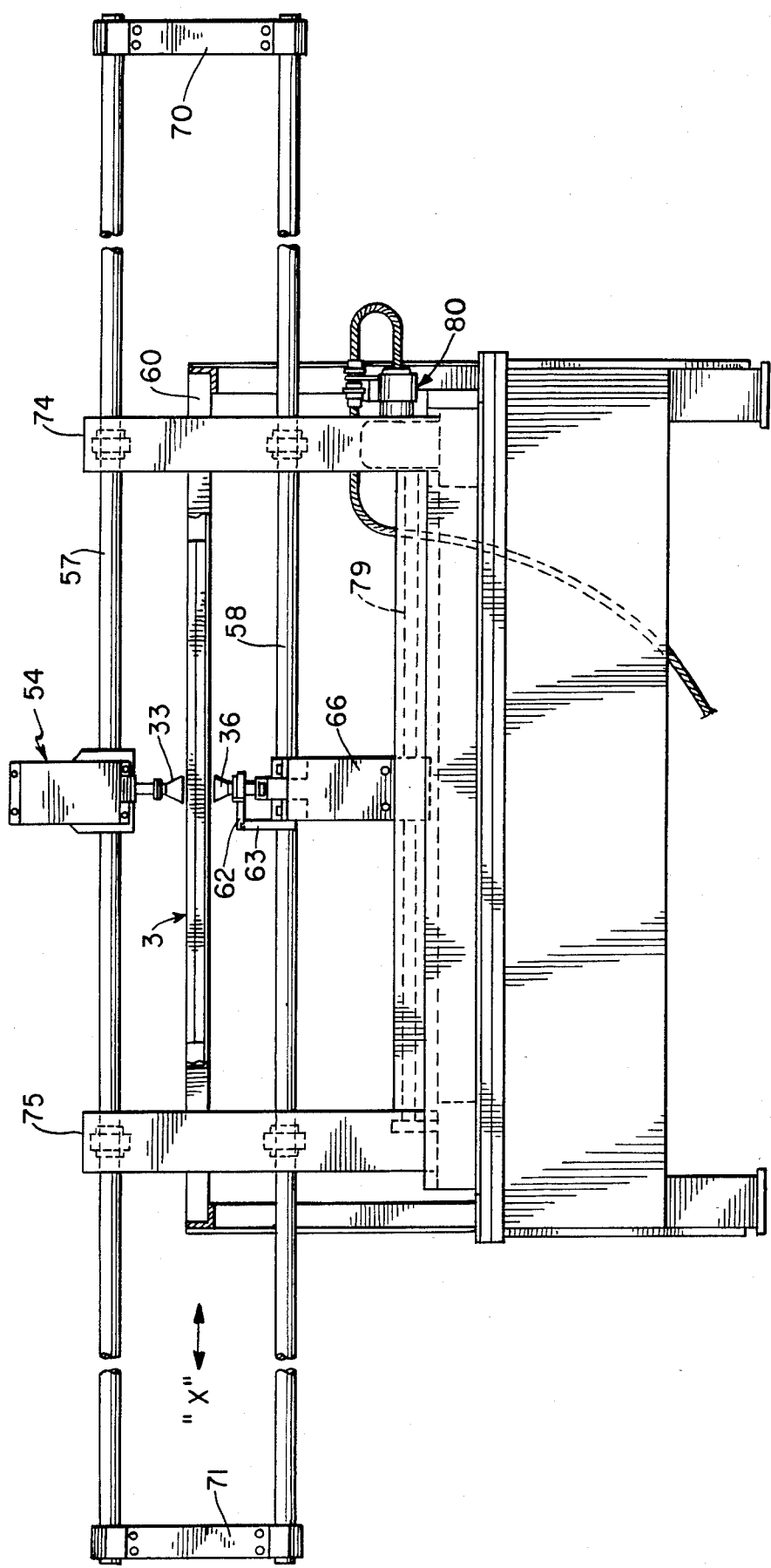

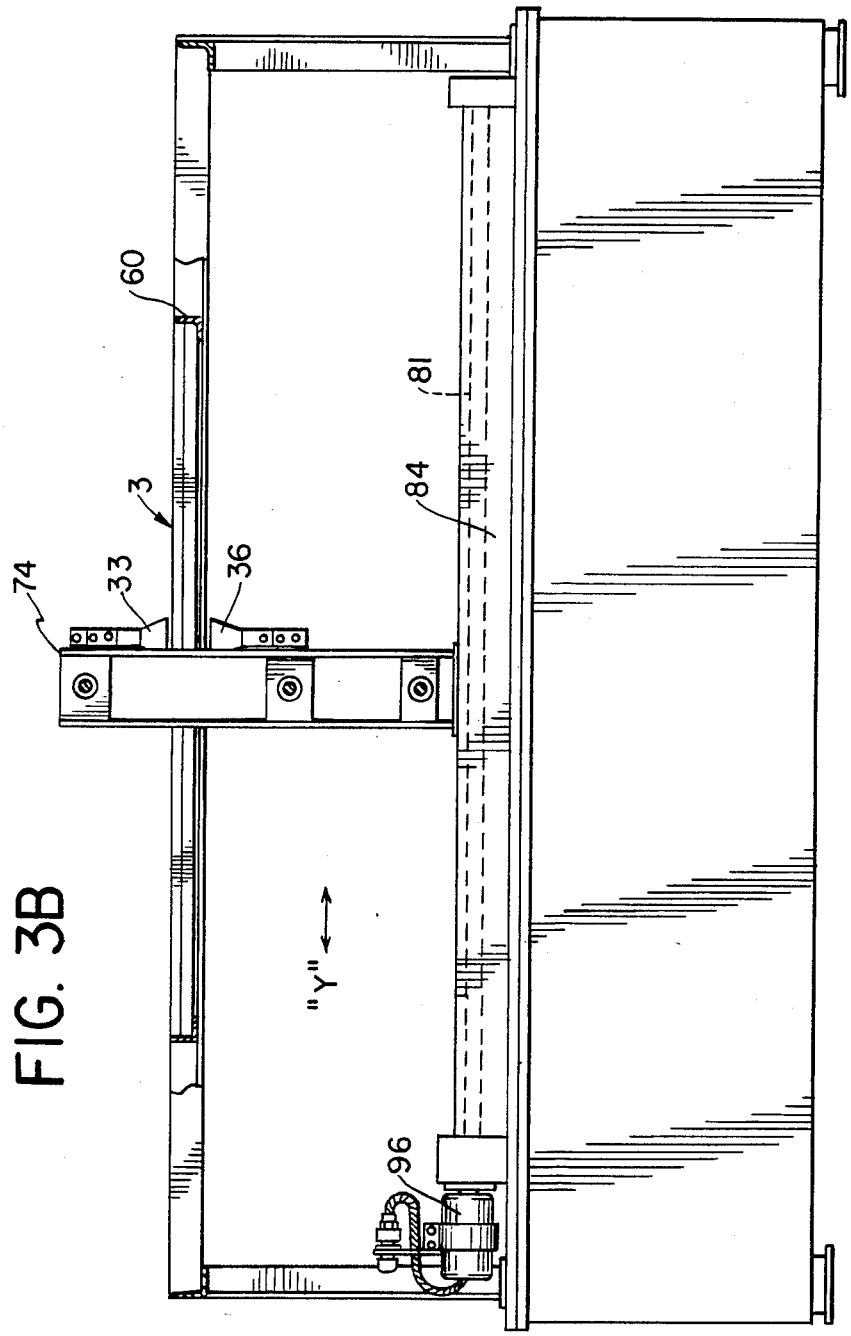

TWO DIMENSIONAL MICROWAVE CHEMICAL FLOOD TESTING MEANS AND METHOD

BACKGROUND OF THE INVENTION

1. Field of the Invention

The present invention relates to means and methods for chemical flood testing and, more particularly, to chemical flood testing using microwave energy.

2. Description of the Prior Art

Chemical flood core testing in a linear or single direction is disclosed and described in U.S. patent application Ser. No. 336,142 now U.S. Pat. No. 4,490,676 12/25/84 and application Ser. No. 336,136, now U.S. Pat. No. 4,482,634 11/13/84 both filed on Dec. 31, 1981 and assigned to Texaco Inc., assignee of the present invention. The practice heretofore has been to take the linear flow data from a long core flood test and through known mathematical techniques predict a two dimensional chemical flood in a pattern in an oil reservoir. The present invention is capable of actually measuring a two dimensional chemical flood through a porous medium that may be used to either supplement and prove the predictions based on the linear flow testing or it may be used independently of the predictions as another step in chemical flood testing.

SUMMARY OF THE INVENTION

The means and method of a two dimensional chemical flood testing includes evacuating a porous medium contained in a test cell. The evacuated porous medium is then irradiated with a beam of microwave energy in said test cell in a plurality of predetermined locations of said test cell defined by a two-axis coordinate system. The microwave energy that has passed through the porous medium at each location is detected. The porous medium is then filled with brine and the irradiating and detecting steps are repeated. The porous medium is then flooded with crude oil, or its substitute, and again the irradiating and detecting steps are repeated. The porous medium is flooded with brine and, again, the irradiating and detecting steps are repeated. A calibration curve for each location is derived from the detected microwave energy at the location from the prior detecting steps at the location. The porous medium while being flooded with a chemical flood system at a predetermined flow rate is periodically subjected to the irradiating and detecting steps so that the test cell is periodically scanned in two directions by microwave energy. A two dimensional pattern of the chemical flooding is derived for each scan in accordance with the detected microwave energy at each location for the scan and the calibration curves.

The foregoing and other objects and advantages of the invention will appear more fully hereinafter from consideration of the detailed description which follows, taken together with the accompanying drawings wherein one embodiment of the present invention is illustrated by way of example. It is to be expressly understood, however, that the drawings are for illustration purposes only and are not to be construed as defining the limits of the invention.

DESCRIPTION OF THE DRAWINGS

FIGS. 3A and 3B are an end view and a side view, respectively, of the mechanical portion of the microwave chemical flood scanner shown in FIG. 1.

DESCRIPTION OF THE INVENTION

U.S. patent applications, Ser. Nos. 336,136 and 336,142, filed on Dec. 31, 1981 by the inventors of the present invention which is assigned to Texaco Inc., assignee of the present invention, relate to chemical flood evaluations being made on cores of an earthen reservoir to evaluate the chemicals used. It is possible with the information from those analyses to project and predict a flood pattern of a particular chemical flood system through a reservoir. A chemical flood system is a flood system using one or more liquid chemicals in conjunction with a drive liquid. The drive may be a liquid or it may be water or brine. Often, a five-spot operation is used in enhanced oil recovery; i.e., four wells defining substantially a horizontal square with a fifth well in the center of the square. Thus, with a given injection well, there is a three dimensional flow of chemicals and drive liquid through the reservoir vertical, traverse and longitudinal. Since the chemical flood analyses of the aforementioned U.S. applications deal with only one dimension or direction, the present invention using two-dimensional monitoring yields more information in regard to a two dimensional flow pattern that the liquids will follow.

Figure 1:
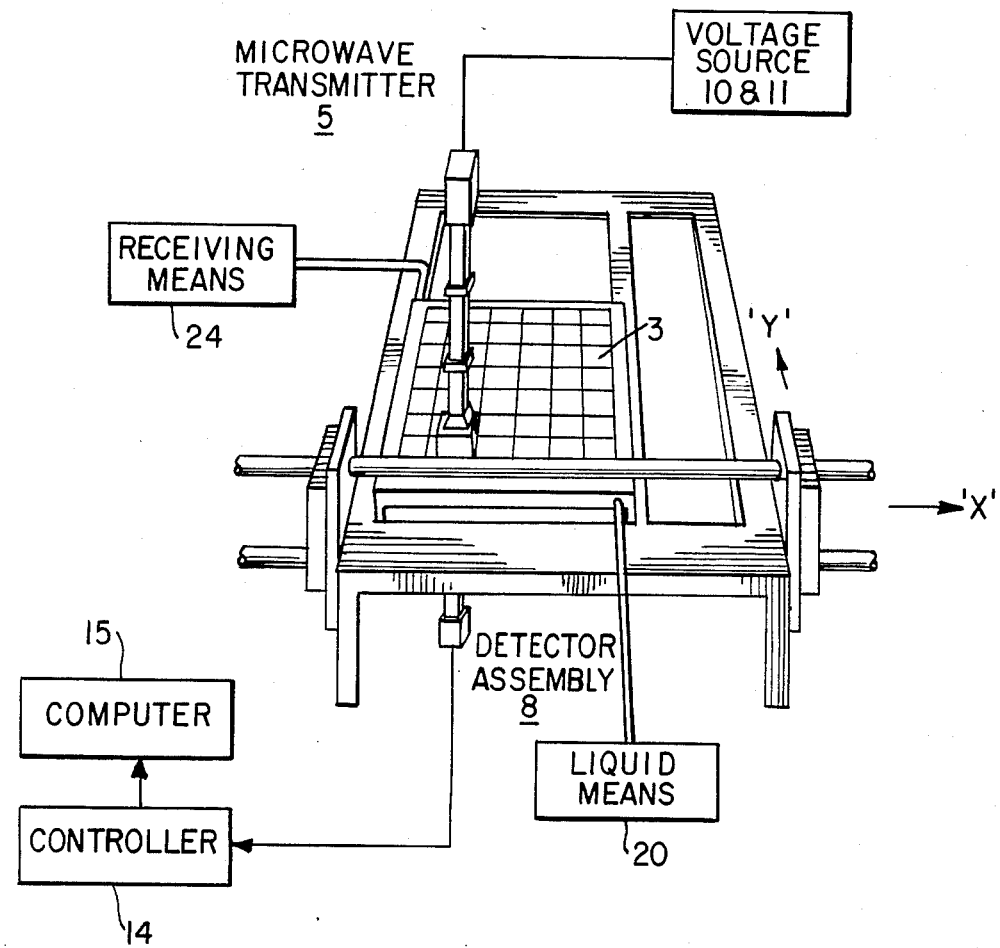
FIG. 1 is a pictorial representation in combination with a simplified block diagram of a microwave chemical flood scanner constructed in accordance with the present invention.

With regard to FIG. 1, a rectangular porous medium in a test cell 3, and any liquid flowing through it, is subjected to a beam of microwave energy by a microwave transmitter 5, as hereinafter explained, which passes through the test cell 3 and is detected by detector assembly 8. Microwave energy is herein defined as being electromagnetic energy provided at a microwave frequency. Microwave transmitter 5 receives the necessary operating voltages from voltage sources 10 and 11. The output from detector assembly 8 is provided to a controller 14 which provides information to computer 15.

Liquid means 20 causes different liquids at different times to be injected into test cell 3, as hereinafter explained, at a predetermined velocity which will eventually flow through test cell 3 and enter receiving means 24. As the liquid passes through test cell 3, microwave transmitter 5 and detector assembly 8 are maintained in fixed relationship to each other but are moveable in an x direction and in a y direction under the control of controller 14, and the movement is repeated during the flowing of the liquids through test cell 3. All of the foregoing will be described hereinafter in greater detail.

Figure 2:
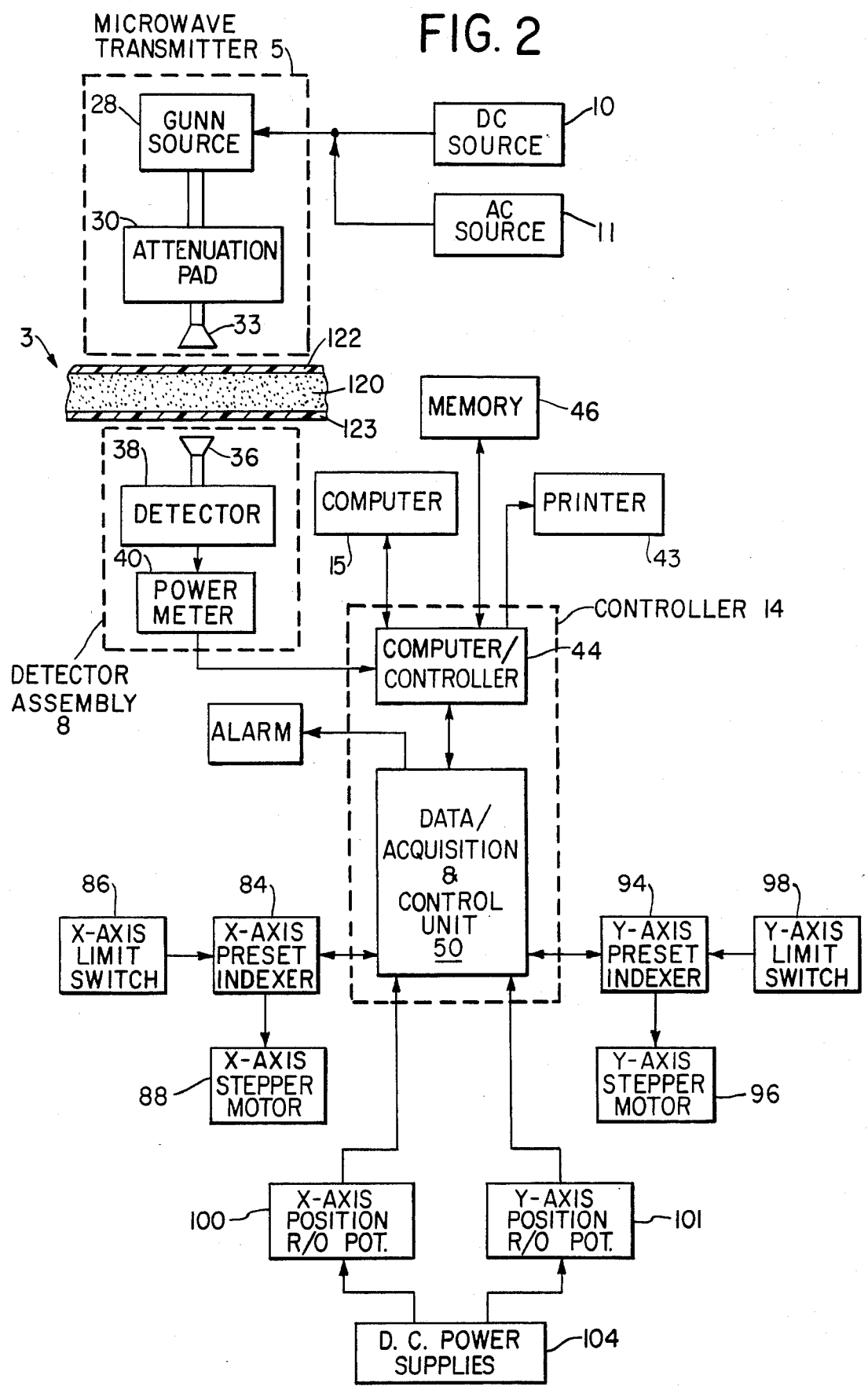
FIG. 2 is a detailed block diagram of the electrical portion of the microwave chemical flood scanner shown in FIG. 1.

With reference to FIG. 2, microwave transmitter 5 includes a Gunn source 28 receiving a DC voltage from DC source 10 and an AC voltage having a preferred frequency of 1 KHz from AC source 11 and provides microwave energy. Gunn source 28 may be of a type that is manufactured by Racon, Inc. as their part number 10014-102-02. The microwave energy is provided at a preferred frequency of 10.525 GHz whose amplitude oscillates at the 1 KHz frequency. Source 28 provides the microwave energy to an attenuator 30 which in turn provides the microwave energy to a horn antenna 33 which provides the beam of microwave energy. It should be noted that a horn antenna is used because Gunn source 28 is being operated in an X-band mode mainly in 8.2 to 12.4 GHz.

It may be desired to operate Gunn source 28 at a preferred frequency of 24.125 GHz which is in the K-band range of frequency namely 18.0 to 26.5 GHz. Operation in the K-band mode makes monitoring of the liquid passing through test cell 3 more independent of temperature and salinity. The determination of whether to use X-band or K-band is also in part determined by the thickness of the formation being tested. A preferred power output for the X-band is 10 milliwatts or for the K-band, 20 to 100 milliwatts, are safe operating levels. When operating in a K-band, horn antenna 33 is replaced by a dielectric rod antenna and Gunn source 28 is of a type similar to that manufactured by Plessey Optoelectronics and Microwaves, Ltd. as their part GDO131. Further, the AC source may be omitted in K-band operation and an isolator is substituted for attenuation pad 30.

The microwave energy passing through sample cell 3 is received by another horn antenna 36 of detector assembly 8, in X-band mode of operation, or a dielectric rod antenna in a K-band mode, and provided to a diode detector 38 which provides a signal corresponding to the detected microwave energy to a power meter 40. Power meter 40 provides an indication of the detected microwave energy and a measurement signal to controller 14 which in turn provides the measurement signal to computer 15 and to a printer 43. Controller 14 includes a computer/controller 44 connected to power meter 40 and receiving the signals therefrom, and, in turn, provides a signal to printer 43 and to computer 15. Computer 15 may be a general purpose digital computer, the equivalent of International Business Machine Corporation's computer. Computer/controller 44 may be of the type manufactured by Hewlett-Packard as their model number H-P85. Associated with computer/controller 44 is a memory 46 having a two-way communication with computer controller 44. Computer/controller 44 also has two-way communication with data/acquisition and control unit 50 which may be of the type manufactured by Hewlett-Packard as their model number H-P3497A. Data acquisition and control unit 50 utilizes the information from computer/controller 44 to send information necessary to the movement and control of microwave transmitter 5 and detector assembly 8.

Referring back to FIG. 1 and to FIGS. 3A, and 3B, the apparatus of microwave transmitter 5, detector assembly 8, and test cell 3 are mounted on apparatus which is basically a combination of units of the type manufactured by Velmex Inc. under their part numbers B6000 and B4000. The combination of two belt coupled B6000 units and a B4000 unit gives the operation two dimensional movement. A housing 54 houses the Gunn source 28 and attenuation pad 30 and is affixed to a rod 57. The electrical connections to DC source 10 and AC source 11 are not shown. Test cell 3 is mounted on a fixed body 60. Antenna 36 is connected to detector 38 supported by arms 62 and 63 with detector 38 being located in a housing 66 mounted to a rod 58 and engaging a screw rod 79. Rods 57 and 58 are maintained in a fixed relationship to each other by end brackets 70, 71 and are controlled to slide through mountings 74 and 75 so as to move antennae 33 and 36 along one direction (x direction) of sample cell 3 by screw rod 79 driven by a stepper motor 80. Members 74 and 75 are controlled to move in another direction (Y direction) by a stepper motor 96 along slides 81 and 81A (not shown) by screw rods 84 and 84A (not shown), respectively.

Referring again to FIG. 2, data/acquisition and control unit 50 controls an X axis preset indexer 84 and in turn receives information as to its index position. An X axis limit switch 86 provides a signal to X axis preset indexer so as to prevent microwave transmitter 5 and detector assembly 8 from exceeding a predetermined x distance. X axis preset indexer 84 provides a signal to X axis stepper motor 88 to control the positioning of the X axis of microwave transmitter 5 and detector assembly 8. Similarly, data/acquisition and control unit 50 provides a signal to and receives a signal from Y axis preset indexer 94. Indexer 94 also receives a signal from Y axis limit switch 98 so as to prevent microwave transmitter 5 and detector assembly 8 from exceeding a Y direction limit. The Y axis preset indexer provides a signal to Y axis stepper motor 96 to control movement in the Y direction. X axis position readout potentiometer 100 and Y axis position readout potentiometer 101 receive energizing voltages from DC power supplies 104 and provides signals to data/acquisition and control unit 50 corresponding to the location of microwave transmitter 5 and detector assembly 8 in the X direction and in the Y direction, respectively.

Figures 4, 5:
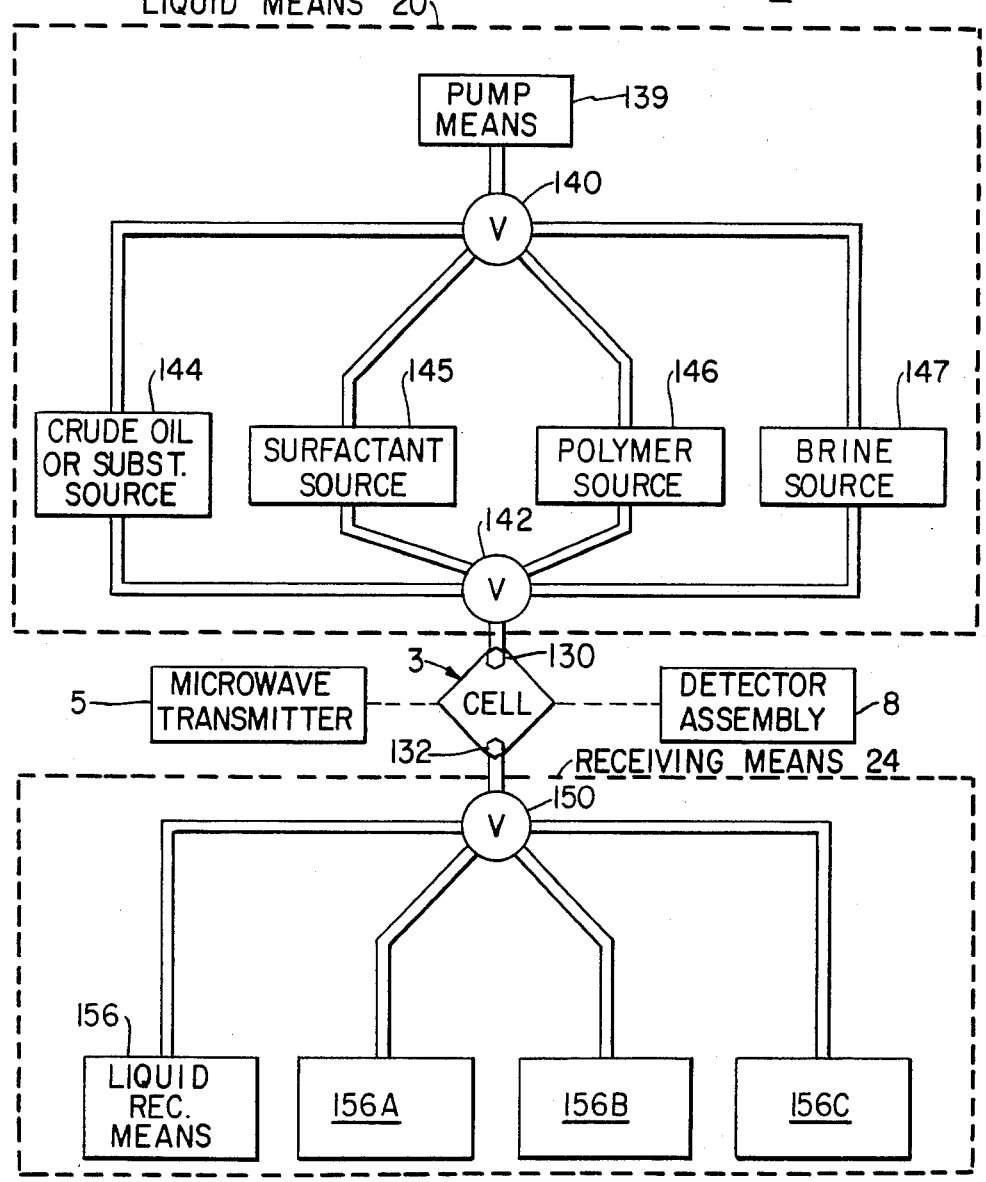
FIG. 4 is a top view of the test cell shown in FIGS. 1 and 2.
FIG. 5 is a simplified block diagram of the hydraulic system of the microwave chemical flood scanner shown in FIG. 1.

With reference to FIG. 2 and FIG. 4, the cross-sectional portion of test cell 3 shows a porous formation 120 coated with epoxy 122 and 123. Formation 120 may be an actual earth formation or it may be a fabricated formation. One such fabricated formation is an oil-wet, homogeneous, synthetic consolidated porous material composed of spherical glass beads epoxed together. A matrix of this type is manufactured under the name, Tegraglas Porous Structures, grade 15, which is the least permeable form currently available, has a very uniform pore size of 16–17 $\mu$m, a permeability of 1–2 darcies, a porosity of about 30%, and a surface area of only 0.057 $m^2/g$. As shown in FIG. 4, the sample cell is substantially square, two opposite corners are chamfered to have a 45° corner, and a simulated wellhead is connected to each chamfered corner. Each wellhead 130 or 132 has internal passageways adapted to accept conventional type chromatograph fittings. The resultant model is $\frac{1}{4}$ of a 5-spot pattern; that is, the center well and one corner well of a conventional 5-spot configuration.

Referring now to FIG. 5, liquid means 20 include pump means 139 which pumps distilled water through valve means 140. Valve means 140 in conjunction with valve means 142 in effect controls which liquid is going to be provided to test cell 3 by way of well 130. In one mode, the output from valve means 140 is provided to a crude oil, or a substitute source 144. One such substitute may be a predetermined mixture of fresh water and 2-propanol. In another mode, valve means 140 provides distilled water to a surfactant source 145, in yet another mode, the output from valve means 140 is provided to a polymer source 146, and in a fourth mode results in valve means 140 output being provided to a brine source 147. Each source, 144, 145, 146 or 147 includes a conventional type free floating piston (not shown) in a container (not shown) having either a crude oil or a substitute, or surfactant, or polymer, or brine. The pumped-in distilled water causes the piston to expel a corresponding amount of liquid (crude oil or its substitute, surfactant, polymer or brine). The output of crude oil source 144, surfactant source 145, polymer source 146 and the brine source 147 are provided to four different inputs of valve means 142. Thus for one mode, pump means 139 in effect pumps crude oil, or its substitute, from crude oil source 144 into test cell 3; in the second mode surfactant from surfactant source 145 is pumped into test cell 3; while in a third mode, pump means 139 in effect pumps polymer from polymer source 146 into test cell 3, and for the fourth mode, brine is pumped into test cell 3.

The liquid from valve means 142 passes through test cell 3 to another valve means 150 in receiving means 24 by way of well 132. Valve means 150 is operated in conjunction with valve means 140 and 142 to pass liquid from test cell 3 to liquid receiving means 156, 156A, 156B or 156C. It should be noted that elements having the same numerical identification with a different suffix are operated and are connected in a similar manner as the element with the same numerical designation without a suffix.

The present invention may be operated in the following manner. Test cell 3 is completely evacuated and the apparatus of the present invention is operated to position microwave transmitter 5 and detector assembly 8 in predetermined locations so as to make microwave measurements at those locations in a predetermined sequence. It does not matter in what sequence the various locations are subjected to the microwave measurements, but obviously it is easier for programing and comparison to use the same sequence whether the test cell 3 is completely evacuated or is in the process of a test. These first measurements correspond to the porous material 120 of test cell 3 being filled only with crude oil. Test cell 3 is then flooded with brine from source 147 through the operation of pump means 139, valve means 140, 142 and 150 and wells 130 and 132, and, a second set of microwave measurements are made and provided to computer 15 so that a second set of measurements correspond to the brine in test cell 3. Pump means 139, valve means 140, 142 and 150 are again operated to inject crude oil, or its substitute, into test cell 3 until only crude oil, or its substitute, leaves test cell 3 and then microwave transmitter 5 and detector assembly 8 are operated to make measurements at the predetermined locations. This third set of measurements corresponds to residual brine to oil at the different locations or in the case of the crude oil substitute, corresponds to an equivalent oil saturation. Pump means 139, valve means 140, 142 and 150 are again operated to inject salt water into test cell 3 until only salt water leaves test cell 3. Microwave transmitter 5 and detector assembly 8 are then operated to make the measurements at the predetermined locations. This fourth set of measurements corresponds to the water flood residual oil at the different locations. The four measurements at each location are used to derive a calibration curve for each location. The calibration curves are generated by computer 15 utilizing conventional curve generation techniques. In some cases, software programs for computer 15 may be purchased from companies that manufactured the computer 15, such as International Business Machine Corporation.

At this point, the actual testing of the chemical flood now commences. It should be noted that in chemical flooding many combinations can be utilized. For example, and this is not truly a chemical flood, brine may be used to drive the oil from the injection well to the producing well, which is a water flood. In chemical flooding techniques a surfactant is used, sometimes driven by brine, or sometimes driven by a polymer. Another alternative to the combination would be a surfactant followed by a polymer driven by brine. Thus, various combinations of liquid chemicals with or without brine may be used in the field. It should be noted that although the term brine is used, it is meant that a water is used, and preferably a water solution with a chemical composition similar to that of the water in the actual oil reservoir or the water that will be used to drive the chemical flood.

In one mode of chemical flooding, pump means 139, valve means 140, 142 and 150 are operated in a sequence so that a slug of surfactant from source 145 followed by a slug of polymer from source 146 and driven by brine is injected into test cell 3 by way of well 130 so that the oil remaining in test cell 3 after the water flood of the calibration process is driven to producing well 132. While this is going on, microwave transmitter 5 and detector assembly 8 are operated in a manner so that they will provide microwave measurements to computer 15 for each location in a predetermined pattern. One such pattern is to divide test cell 3 into a plurality of smaller areas and the microwave transmitter 5 and detector assembly 8 are positioned at each area. Each area is irradiated with microwave energy with detector assembly 8 detecting the energy passing through that area to provide its reading, the sequence being that each area adjacent to well 130 is measured initially and the next adjacent area is read, and so forth progressing away from well 130 so as to scan test cell 3. This scanning operation is repeated throughout the cell 3 will be scanned 20 times in the predetermined sequence during the test time.

The slug sizes of surfactant and polymer are predetermined and may vary from test to test at the desire of the operator. The flow rate of the chemical flood is scaled to approach the reservoir flood velocity. The typical reservoir flood velocity might be one foot per day. Computer 15 can then provide either or both a printout of the microwave readings at each location for each scan and a two-dimensional graph of test cell 3 showing the distribution of the oil as it moves through test cell 3. Again, each graph or plot would be made after each scan during the chemical flood test. It is also feasible to generate the plots or graphs at the end of the chemical flood test since the data is stored during testing.

The present invention as hereinbefore described is a microwave scanner that monitors the chemical flooding of a test cell representative of one quarter of a five spot enhanced oil recovery operation. The present invention is not restricted to five spot operation analysis, but is also applicable to any enhanced oil recovery utilizing chemical flooding with at least an injection well and a producing well.

What is claimed is:
1. A microwave chemical flood scanner comprising:
   a test cell having an entry port and an exit port and containing a porous medium, said test cell having side dimensions which are substantially greater than a thickness dimension of said test cell,
   liquid source means for providing different liquids to said entry port, means for receiving the different liquids from said exit port, transmitter means for providing a beam of microwave energy when energized, receiver means, spatially related to said transmitter means in a manner so that said test cell may be permitted to be interposed between said transmitting means and said receiving means, for receiving a beam of microwave energy after it has passed through said test cell and providing a signal corresponding to a characteristic of at least one liquid in said porous medium in said test cell, means for energizing said transmitting means, means for moving said transmitting means and said receiving means while maintaining their spatial relationship in a manner so that the beam of microwave energy will pass through said test cell at a plurality of predetermined locations that define a two dimensional pattern on said test cell, calibration curve means for deriving and storing a calibration curve for each predetermined location, and means for providing a graphical representation of the liquid content of said porous medium in said test cell in accordance with the signal from the receiving means, stored calibration curves, and the positioning of the transmitter means and receiver means in relation to the locations on the test cell;

said moving means includes first mounting means for having said test cell mounted upon it for holding said test cell in a fixed position, second and third mounting means, for having the transmitter means mounted on the second mounting means and for having the receiving means mounted on the third mounting means in a manner so that they are aligned with each other and having sufficient space between them so that said test cell may be interposed between said transmitter means and said receiver means, first means for moving said second and third mounting means in unison along an X axis, fourth and fifth mounting means having the first moving means mounted thereon, second means for moving the fourth and fifth mounting means along a Y axis, which is perpendicular to the X axis, and means for controlling the movement of the second and third mounting means and the fourth and fifth mounting means so that the transmitter means and the receiver means will stop temporarily at predetermined locations on the test cell for the microwave irradiation through the porous medium at that location; and said liquid means includes:

pump means for pumping a non-corrosive liquid, a crude oil, or a substitute, source, a surfactant source, a polymer source and a brine source, first valve means connecting said pump means to said crude oil source, to said surfactant source, to said polymer source and to said brine source for controlling the liquid provided by said pump means to be provided to either the crude oil or substitute source, the surfactant source, the polymer source, or the brine source so as to displace crude oil from the crude oil source, surfactant from the surfactant source, polymer from the polymer source, or brine from the brine source;

second valve means connected to the crude oil source, to the surfactant source, to the polymer source, to the brine source and to the entry port of said test cell and cooperating with the first valve means for directing the brine, the polymer, the surfactant, or the crude oil or its substitute, into said test cell; and the liquid receiving means includes:

third valve means for cooperating with said first and second valve means, and connected to the exit port of said test cell three for providing the liquid flowing from the sample cell to an appropriate container means or a plurality of container means.

2. A microwave scanner as described in claim 1 in which the transmitter means provides a beam of microwave energy at a frequency in the X-band frequency.

3. A microwave scanner as described in claim 2 in which the transmitter means is energized by the energizing means at each location and not while it is moving from location to location.

4. A microwave scanner as described in claim 1 in which the microwave transmitter means provides a beam of microwave energy at a frequency in the K-band.

5. A microwave means as described in claim 4 in which the transmitter means is energized by the energizing means at each location and not while it is moving from location to location.

* * * * *